(12) United States Patent
Kawakami

(10) Patent No.: US 8,668,659 B2
(45) Date of Patent: Mar. 11, 2014

(54) FINGER MOTION ASSISTING APPARATUS

(75) Inventor: Takashi Kawakami, Ehime (JP)

(73) Assignee: Panasonic Corporation, Osaka (JP)

( * ) Notice: Subject to any disclaimer, the term of this patent is extended or adjusted under 35 U.S.C. 154(b) by 251 days.

(21) Appl. No.: 12/755,554

(22) Filed: Apr. 7, 2010

(65) Prior Publication Data

US 2010/0249676 A1 Sep. 30, 2010

(30) Foreign Application Priority Data

Sep. 11, 2008 (JP) .................................. 2008-233930

(51) Int. Cl.
*A61H 1/02* (2006.01)
(52) U.S. Cl.
USPC .......................................................... 601/40
(58) Field of Classification Search
USPC ........... 601/40, 5, 23, 33; 600/595; 602/5, 20,
602/21, 22; 315/568.21; 294/106; 623/24,
623/64; 901/30, 31, 32, 33, 34, 35, 36;
482/44, 47, 48
See application file for complete search history.

(56) References Cited

U.S. PATENT DOCUMENTS

| | | | | |
|---|---|---|---|---|
| 2,885,686 A | * | 5/1959 | Giaimo | 623/24 |
| 4,167,044 A | * | 9/1979 | Girard | 623/63 |
| 4,834,761 A | * | 5/1989 | Walters | 623/26 |
| 5,807,376 A | * | 9/1998 | Viola et al. | 606/1 |

FOREIGN PATENT DOCUMENTS

| | | |
|---|---|---|
| JP | 07-204233 A | 8/1995 |
| JP | 2000-325375 A | 11/2000 |
| JP | 2002-345861 A | 12/2002 |
| JP | 2002-345861 A | 12/2002 |
| JP | 2007-313093 A | 12/2007 |

OTHER PUBLICATIONS

Scientific American, Oct. 1998, Figure at bottom of p. 44.*

* cited by examiner

*Primary Examiner* — Jackie Ho
*Assistant Examiner* — Mark Wardas
(74) *Attorney, Agent, or Firm* — RatnerPrestia

(57) ABSTRACT

It is an object of the present invention to provide a finger motion assisting apparatus that can be attached to a user without precise positioning or aligning the mechanism parts and substantially without size-fitting operation caused by physical size difference. According to the finger motion assisting apparatus of the present invention, the wire guide group 30 includes the first wire guide group 31 located on the palm side of the phalanxes 10, and the second wire guide group 32 located on the back side of the phalanxes 10, the wire is fixed to the finger holding member 20 located on the distal phalanx, the wire 40 includes the first wire 41 inserted through the first wire guide group 31, and the second wire 42 inserted through the second wire guide group 32, and the driving unit 53, 54 loosens the second wire 42 when the first wire 41 is pulled, and loosens the first wire 41 when the second wire 42 is pulled.

16 Claims, 16 Drawing Sheets

FINGER MOTION ASSISTING APPARATUS

TECHNICAL FIELD

The present invention relates to a finger motion assisting apparatus that assists a bending and stretching motion of a finger of a user's hand.

BACKGROUND TECHNIQUE

As an apparatus for assisting a bending and stretching motion of a finger of a hand, there is proposed an apparatus that connects or engages mechanism parts such as a joint portion, an arm and a gear with each other, thereby carrying out the bending and stretching motion of a finger (patent document 1).

[Patent Document 1] Japanese Patent Application Laid-open No. 2002-345861

DISCLOSURE OF THE INVENTION

However, this apparatus uses a large number of mechanism parts, and it is difficult to reduce the size of the apparatus while keeping its strength. Further, since the mechanism parts such as the joint portion, the arm and the gear are precisely engaged with each other, the apparatus moves precisely as planned, but it is necessary to precisely position or align the mechanism parts. Further, tolerance to a difference in physical size of a user is narrowed, and there is a problem that the apparatus must be produced in accordance with a size of each user.

Hence, it is an object of the present invention to provide a finger motion assisting apparatus that can be worn on a user without precise positioning or aligning the mechanism parts and substantially without size-fitting operation caused by physical size difference.

A first aspect of the present invention provides a finger motion assisting apparatus including: a finger holding member disposed on an outer periphery of phalanxes including a distal phalanx, a middle phalanx and a proximal phalanx; a wire guide group provided on the finger holding member; a wire inserted through the wire guide group; and a driving unit that pulls or loosens the wire; in which the finger motion assisting apparatus bends and stretches the phalanxes, wherein the wire guide group includes a first wire guide group located on a palm side of the phalanxes, and a second wire guide group located on a back side of the phalanxes, the wire is fixed to the finger holding member located on the distal phalanx, the wire includes a first wire inserted through the first wire guide group, and a second wire inserted through the second wire guide group, and the driving unit loosens the second wire when the first wire is pulled, and loosens the first wire when the second wire is pulled.

According to a second aspect, in the finger motion assisting apparatus of the first aspect, a compression spring is used as the finger holding member.

According to a third aspect, in the finger motion assisting apparatus of the first aspect, the finger holding member includes a palm-side finger holding member disposed on the palm side of the phalanxes, and a back-side finger holding member disposed on the back side of the phalanxes, each of the palm-side finger holding member and the back-side finger holding member includes a plurality of bridge members having the wire guide group, and a pair of connecting members connecting ends of the bridge members with each other, and the connecting member constituting the palm-side finger holding member and the connecting member constituting the back-side finger holding member can be attached to and detached from each other.

According to a fourth aspect, in the finger motion assisting apparatus of the third aspect, an elastic material is used as the connecting member.

According to a fifth aspect, in the finger motion assisting apparatus of the third aspect, the connecting member constituting the palm-side finger holding member and the connecting member constituting the back-side finger holding member are made of elastic material, a wire is used as one of the connecting members, and a C-shaped pipe having an inner diameter that is greater than an outer diameter of the wire is used as the other connecting member.

According to a sixth aspect, in the finger motion assisting apparatus of the fifth aspect, a plurality of slits are formed in the other connecting member in a direction perpendicular to an axis of the other connecting member.

According to a seventh aspect, in the finger motion assisting apparatus of the first aspect, the first wire guide group and the second wire guide group constitute a plurality of rows, and the first wire and the second wire are disposed in correspondence with the respective rows.

According to an eighth aspect, in the finger motion assisting apparatus of the first aspect, at least one wire guide constituting the wire guide group is provided in correspondence with each of the distal phalanx, the middle phalanx and the proximal phalanx.

According to a ninth aspect, in the finger motion assisting apparatus of the first aspect, a warp-preventing member is provided on the finger holding member disposed on the back side of a first joint between the distal phalanx and the middle phalanx astride the first joint, and the warp-preventing member restricts the distal phalanx such that the distal phalanx does not bend backward more than a predetermined angle with respect to the middle phalanx.

According to a tenth aspect, in the finger motion assisting apparatus of the first aspect, a warp-preventing member is provided on the finger holding member disposed on the back side of a second joint between the middle phalanx and the proximal phalanx astride the second joint, and the warp-preventing member restricts the middle phalanx such that the middle phalanx does not bend backward more than a predetermined angle with respect to the proximal phalanx.

According to an eleventh aspect, in the finger motion assisting apparatus of the first aspect, a compression/warp-preventing member is provided on the finger holding member astride a joint of the phalanxes, the compression/warp-preventing member includes a plurality of fixing units and a movable unit connecting the fixing units with each other, the compression/warp-preventing member restricts a backward bending motion of the phalanxes caused by interference between the fixing units, and restricts compression toward a metacarpal bone with respect to the phalanxes.

According to a twelfth aspect, in the finger motion assisting apparatus of the first aspect, a joint lock mechanism is provided on at least one of a back side and a palm side of a third joint between the proximal phalanx and a metacarpal bone astride the third joint, and the joint lock mechanism restricts the proximal phalanx such that the proximal phalanx does not bend toward the palm side more than a predetermined angle with respect to the metacarpal bone.

According to a thirteenth aspect, in the finger motion assisting apparatus of the twelfth aspect, the bending restriction of the proximal phalanx with respect to the metacarpal bone is released by moving the joint lock mechanism toward the metacarpal bone.

According to a fourteenth aspect, the finger motion assisting apparatus of the first aspect further includes a plate for supporting a metacarpal bone, and a joint lock mechanism connected to the plate between the proximal phalanx and the plate, wherein the joint lock mechanism restricts the proximal phalanx such that the proximal phalanx does not bend toward the palm side more than a predetermined angle with respect to the metacarpal bone.

According to a fifteenth aspect, in the finger motion assisting apparatus of the fourteenth aspect, the bending restriction of the proximal phalanx with respect to the metacarpal bone is released by releasing the connection between the joint lock mechanism and the plate.

According to a sixteenth aspect, the finger motion assisting apparatus of the first aspect further includes a wrist fixing tool for restricting a joint motion of a wrist, wherein the wrist fixing tool comprise a first wire guide for the wrist fixing tool through which the first wire is inserted, and a second wire guide for the wrist fixing tool through which the second wire is inserted.

According to the present invention, since the bending and stretching motion of the finger is carried out by pulling the wires respectively provided on the back side and the palm side of the phalanxes, the apparatus can be reduced in size and weight as compared with an apparatus using mechanism parts such as a gear and a pulley.

According to the invention, since the compression spring is used, a neutral axis of the spring matches with a center axis of the finger, a sufficient driving force can be generated even if portions close to the back side or palm side of the finger are pulled, deviation with respect to the finger can be suppressed to a low level when the finger bends or stretches, a comfortable wearing feeling can be obtained, and since the bending position is not fixed, it is unnecessary to carry out the precisely alignment.

According to the invention, since the finger holding member can be attached or detached while dividing the finger holding member into two, i.e., the palm side portion and the back side portion, the finger holding member can easily be attached to the fingers. The finger holding members made of elastic material are disposed on both side surfaces of a center of the finger, and even if the finger bends or stretches, a length of a path between the finger and the spring portion is not varied, and no deviation is generated.

According to the finger motion assisting apparatus of the first aspect of the invention, the wire guide group includes the first wire guide group located on the palm side of the phalanxes, and the second wire guide group located on the back side of the phalanxes, the wire is fixed to the finger holding member located on the distal phalanx, the wire includes the first wire inserted through the first wire guide group, and the second wire inserted through the second wire guide group, and the driving unit loosens the second wire when the first wire is pulled, and loosens the first wire when the second wire is pulled. With this embodiment, since the finger bends and stretches by pulling the wires provided on both the back side and the palm side of the phalanxes, the apparatus can be reduced in size and weight as compared with an apparatus using mechanism parts such as a gear and a pulley.

According to the second aspect of the invention, in the finger motion assisting apparatus of the first aspect, the compression spring is used as the finger holding member. With this embodiment, by using the compression spring, a neutral axis of the spring matches with a center axis of the finger, a sufficient driving force can be generated even if portions close to the back side or palm side of the finger are pulled, deviation with respect to the finger can be suppressed to a low value when the finger bends or stretches, a comfortable wearing feeling can be obtained, and since the bending position is not fixed, it is unnecessary to carry out the precisely alignment.

According to the third aspect of the invention, in the finger motion assisting apparatus of the first aspect, the finger holding member includes a palm-side finger holding member disposed on the palm side of the phalanxes, and a back-side finger holding member disposed on the back side of the phalanxes, each of the palm-side finger holding member and the back-side finger holding member includes a plurality of bridge members having the wire guide group, and a pair of connecting members connecting ends of the bridge members with each other, and the connecting member constituting the palm-side finger holding member and the connecting member constituting the back-side finger holding member can be attached to and detached from each other. With this embodiment, since the finger holding member can be attached or detached while dividing the finger holding member into two, i.e., the palm side portion and the back side portion, the finger holding member can easily be attached to the fingers.

According to the fourth aspect of the invention, in the finger motion assisting apparatus of the third aspect, the elastic material is used as the connecting member. With this embodiment, the finger holding members made of elastic material are disposed on both side surfaces of the center of the finger, and even if the finger bends or stretches, the length of the path between the finger and the spring portion is not varied, and no deviation is generated.

According to the fifth aspect of the invention, in the finger motion assisting apparatus of the third aspect, the connecting member constituting the palm-side finger holding member and the connecting member constituting the back-side finger holding member are made of elastic material, the wire is used as one of the connecting members, and the C-shaped pipe having an inner diameter that is greater than an outer diameter of the wire is used as the other connecting member. With this embodiment, the wire can slide on the C-shaped pipe, and the two-divided finger holding members can easily be attached.

According to the sixth aspect of the invention, in the finger motion assisting apparatus of the fifth aspect, the plurality of slits are formed in the other connecting member in the direction perpendicular to an axis of the other connecting member. With this embodiment, since the connecting member is the C-shaped pipe, the rigidity is enhanced, and the bending characteristics can be enhanced by providing the plurality of slits.

According to the seventh aspect of the invention, in the finger motion assisting apparatus of the first aspect, the first wire guide group and the second wire guide group constitute the plurality of rows, and the first wire and the second wire are disposed in correspondence with the respective rows. With this embodiment, since the plurality of wires are provided on the back side and the palm side, it is possible to assist the stable bending and stretching motion.

According to the eighth aspect of the invention, in the finger motion assisting apparatus of the first aspect, at least one wire guide constituting the wire guide group is provided in correspondence with each of the distal phalanx, the middle phalanx and the proximal phalanx. With this embodiment, since the pulling force of the wire, i.e., the bending force is applied to the position of the wire guide, it is possible to smoothly bend and stretch the finger by providing the wire guides in correspondence with the distal phalanx, the middle phalanx and the proximal phalanx, respectively.

According to the ninth aspect of the invention, in the finger motion assisting apparatus of the first aspect, the warp-preventing member is provided on the finger holding member disposed on the back side of the first joint between the distal phalanx and the middle phalanx astride the first joint, and the warp-preventing member restricts the distal phalanx such that the distal phalanx does not bend backward more than the predetermined angle with respect to the middle phalanx. With this embodiment, it is possible to prevent the backward warp of the first joint to which an especially large force is adversely applied.

According to the tenth aspect of the invention, in the finger motion assisting apparatus of the first aspect, the warp-preventing member is provided on the finger holding member disposed on the back side of the second joint between the middle phalanx and the proximal phalanx astride the second joint, and the warp-preventing member restricts the middle phalanx such that the middle phalanx does not bend backward more than the predetermined angle with respect to the proximal phalanx. With this embodiment, the safety can be enhanced.

According to the eleventh aspect of the invention, in the finger motion assisting apparatus of the first aspect, the compression/warp-preventing member is provided on the finger holding member astride the joint of the phalanxes, the compression/warp-preventing member includes the plurality of fixing units and the movable unit connecting the fixing units with each other, the compression/warp-preventing member restricts the backward bending motion of the phalanxes caused by interference between the fixing units, and restricts compression toward a metacarpal bone with respect to the phalanxes. With this embodiment, it is possible to more reliably prevent the compression and the backward warp.

According to the twelfth aspect of the invention, in the finger motion assisting apparatus of the first aspect, the joint lock mechanism is provided on at least one of the back side and the palm side of the third joint between the proximal phalanx and the metacarpal bone astride the third joint, and the joint lock mechanism restricts the proximal phalanx such that the proximal phalanx does not bend toward the palm side more than the predetermined angle with respect to the metacarpal bone. With this embodiment, it is possible to assist the bending and stretching motion of especially the middle phalanx.

According to the thirteenth aspect of the invention, in the finger motion assisting apparatus of the twelfth aspect, the bending restriction of the proximal phalanx with respect to the metacarpal bone is released by moving the joint lock mechanism toward the metacarpal bone. With this embodiment, it is possible to assist the bending and stretching motion of especially the proximal phalanx.

According to the fourteenth aspect of the invention, the finger motion assisting apparatus of the first aspect further includes the plate for supporting the metacarpal bone, and the joint lock mechanism connected to the plate between the proximal phalanx and the plate, wherein the joint lock mechanism restricts the proximal phalanx such that the proximal phalanx does not bend toward the palm side more than the predetermined angle with respect to the metacarpal bone. With this embodiment, it is possible to assist the bending and stretching motion of especially the middle phalanx.

According to the fifteenth aspect of the invention, in the finger motion assisting apparatus of the fourteenth aspect, the bending restriction of the proximal phalanx with respect to the metacarpal bone is released by releasing the connection between the joint lock mechanism and the plate. With this embodiment, it is possible to assist the bending and stretching motion of especially the proximal phalanx.

According to the sixteenth aspect of the invention, the finger motion assisting apparatus of the first aspect further includes the wrist fixing tool for restricting the joint motion of the wrist, wherein the wrist fixing tool comprise the first wire guide for the wrist fixing tool through which the first wire is inserted, and the second wire guide for the wrist fixing tool through which the second wire is inserted. With this embodiment, since no member is provided on the palm, it is possible to enhance the wearing feeling.

BEST MODE FOR CARRYING OUT THE INVENTION

Embodiments of the finger motion assisting apparatus according to the present invention will be explained below.

Figure 1:
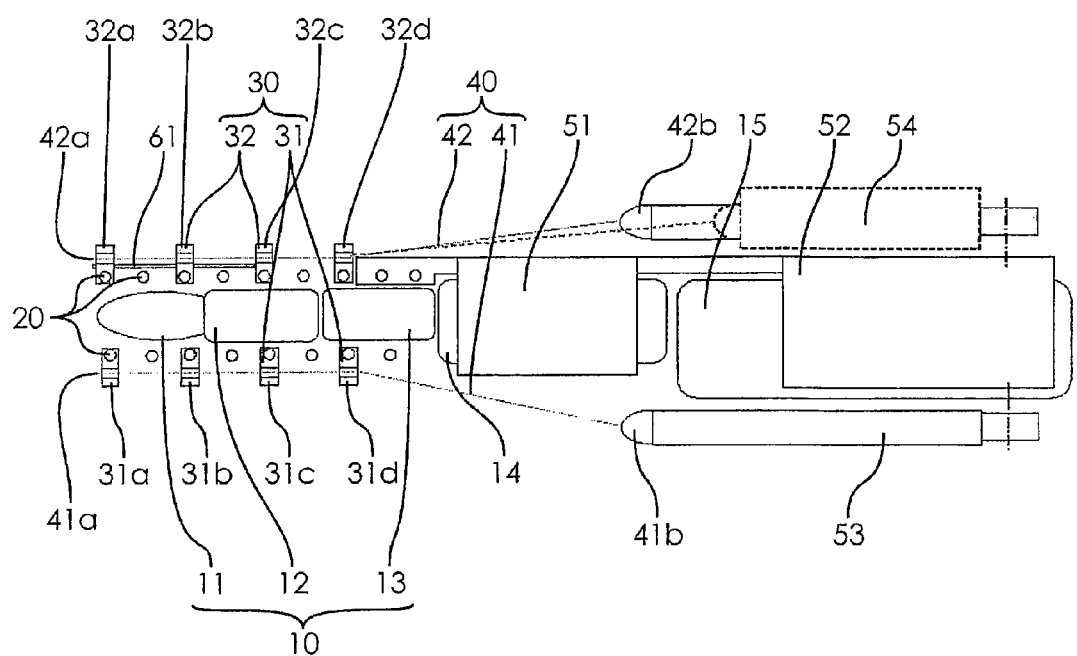
FIG. 1 is a side view showing a structure of a finger motion assisting apparatus according to an embodiment of the present invention in its stretched state.
Figure 2:
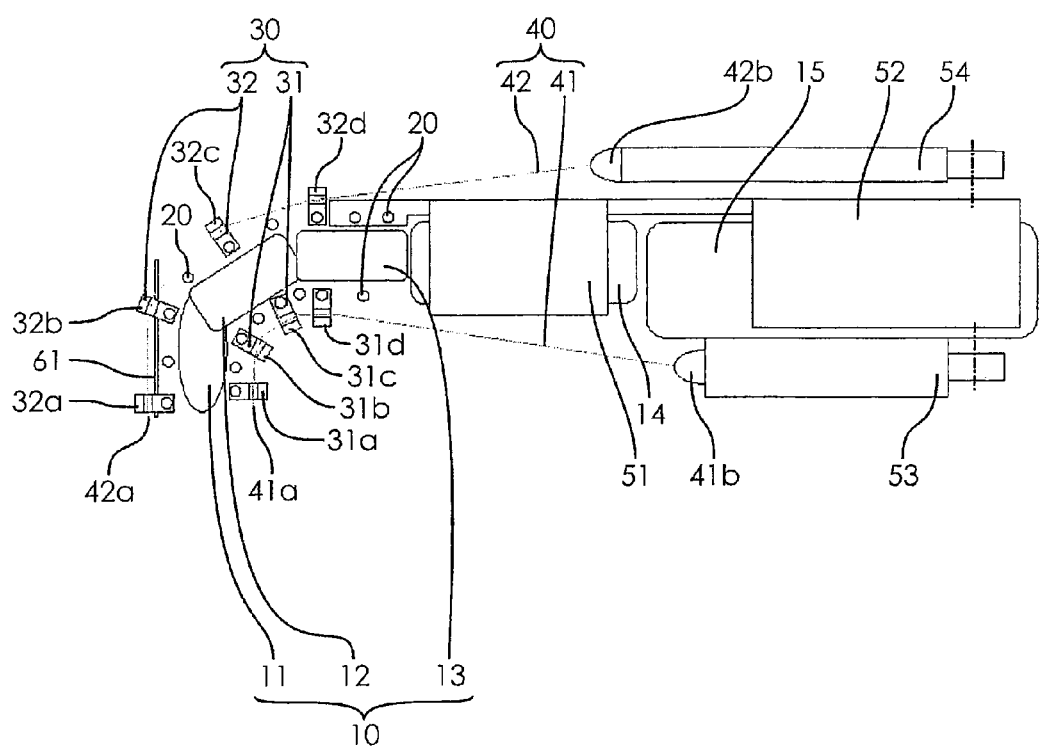
FIG. 2 is a side view showing a structure of the apparatus in its bent state.
Figure 3:
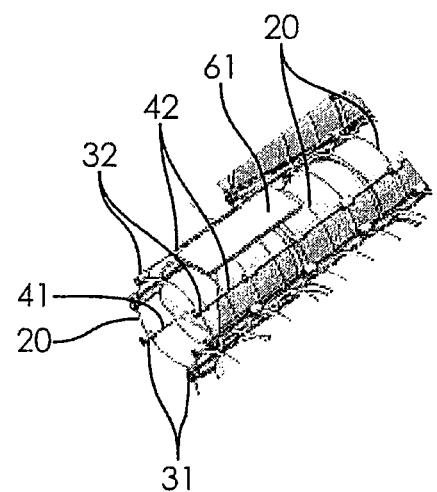
FIG. 3 is a perspective view of an essential portion of the apparatus.

FIG. 1 is a side view showing a structure of the finger motion assisting apparatus in its stretched state according to one embodiment of the present invention. FIG. 2 is a side view showing a structure of the apparatus in its bent state. FIG. 3 is a perspective view of an essential portion of the apparatus.

According to the finger motion assisting apparatus of the embodiment, a finger holding member 20 is disposed around an outer periphery of phalanxes 10 that include a distal phalanx 11, a middle phalanx 12 and a proximal phalanx 13, and the finger holding member 20 includes a wire guide group 30. A compression spring is used as the finger holding member 20. The wire guide group 30 includes a first wire guide group 31 located at the phalanxes 10 on a side of a palm, and a second wire guide group 32 located at the phalanxes 10 on a side of a back.

Wires 40 are inserted through the wire guide group 30. The wires 40 include a first wire 41 inserted through the first wire guide group 31, and a second wire 42 inserted through the second wire guide group 32.

One end of the finger holding member 20 is held by a palm plate 51 that is fixed at a position of a metacarpal bone 14. An arm plate 52 is disposed at a position of a front arm 15. The arm plate 52 is provided with driving units 53 and 54 that pull or loosen the wires 40.

One end 41a and one end 42a of the wires 40 are fixed to the finger holding member 20 located at the distal phalanx 11, and the other end 41b and other end 42b are connected to the driving units 53 and 54, respectively. In this embodiment, the one end 41a and 42a of the wires 40 are fixed to the finger holding member 20 through wire guides 31a and 32a located at the distal phalanx 11.

At least one wire guide constituting the wire guide group 30 is provided in correspondence with each of the distal phalanx 11, the middle phalanx 12 and the proximal phalanx 13. In FIGS. 1 and 2, wire guides 31a, 31b, 32a and 32b correspond to the distal phalanx 11, wire guides 31c and 32c correspond to the middle phalanx 12, and wire guides 31d and 32d correspond to the proximal phalanx 13.

A warp-preventing member 61 is provided on the finger holding member 20 disposed on the back side of the first joint between the distal phalanx 11 and the middle phalanx 12 astride the first joint. The warp-preventing member 61 restrains the distal phalanx 11 such that the distal phalanx does not bend backward with respect to the middle phalanx 12 more than a predetermined angle.

Although it is not illustrated in the drawings, the warp-preventing member 61 may be provided on the finger holding member 20 on the back side of the second joint between the middle phalanx 12 and the proximal phalanx 13 astride the second joint.

FIG. 1 shows a state where the second wire 42 is pulled, the first wire 41 is loosened and the finger of the hand stretches. The driving units 53 and 54 use, as actuators, artificial muscles that extend and contract at least in their longitudinal directions by supplying or discharging gas, liquid, solid material or a mixture thereof. Although it is not illustrated in the drawings, the finger motion assisting apparatus includes power sources that contract the artificial muscles that are the driving units 53 and 54.

Even if a force for pulling the second wire 42 is too strong, since the warp-preventing member 61 is provided on the finger holding member 20 on the back side of the first joint between the distal phalanx 11 and the middle phalanx 12, the finger holding member 20 is not compressed at a position where the warp-preventing member 61 is provided, and the distal phalanx 11 does not bend backward with respect to the middle phalanx 12.

FIG. 2 shows a state where the first wire 41 is pulled, the second wire 42 is loosened and the finger of the hand bends. In this embodiment, since the wire guides 31d and 32d on the side of the driving units 53 and 54 are disposed at the positions of the proximal phalanx 13, the distal phalanx 11 and the middle phalanx 12 bend but the proximal phalanx 13 does not bend.

FIG. 3 shows the warp-preventing member 61. As shown in FIG. 3, the warp-preventing member 61 is formed from a plate member having a predetermined length, and is fixed to the finger holding member 20.

As shown in FIG. 3, the first wire guide groups 31 and the second wire guide group 32 are arranged in two rows. The first wire 41 and the second wires 42 are arranged in correspondence with these rows.

Although the first wire guide groups 31 and the second wire guide group 32 are arranged in two rows, they may be arranged in three or more rows.

Next, other embodiments of the finger motion assisting apparatus of the present invention will be explained.

Figure 4:
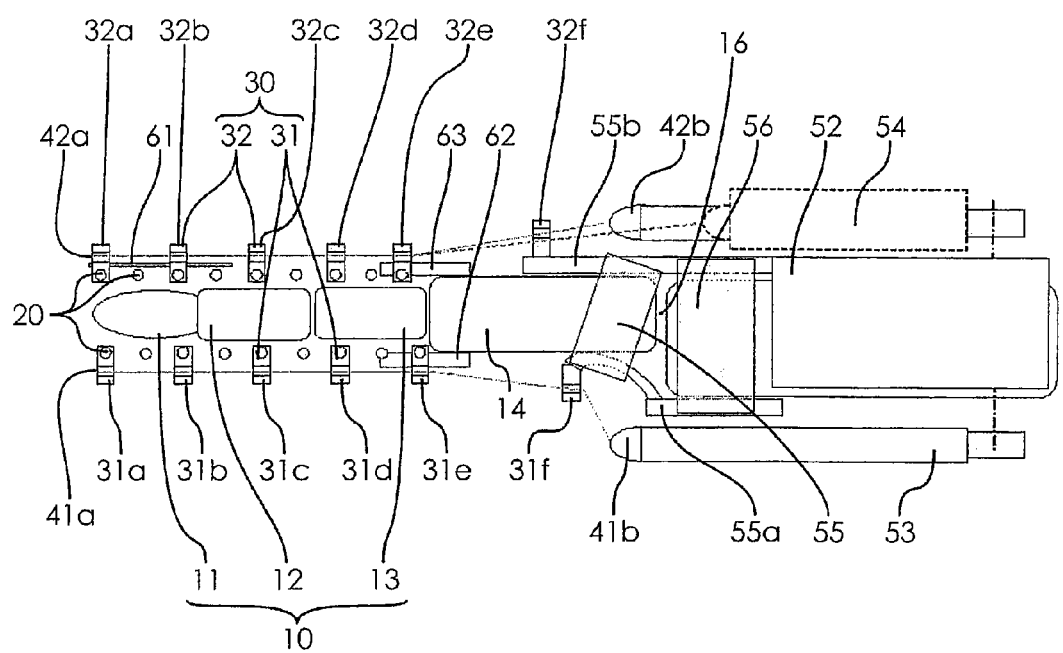
FIG. 4 is a side view showing a structure of a finger motion assisting apparatus according to another embodiment of the invention in its stretched state.
Figure 5:
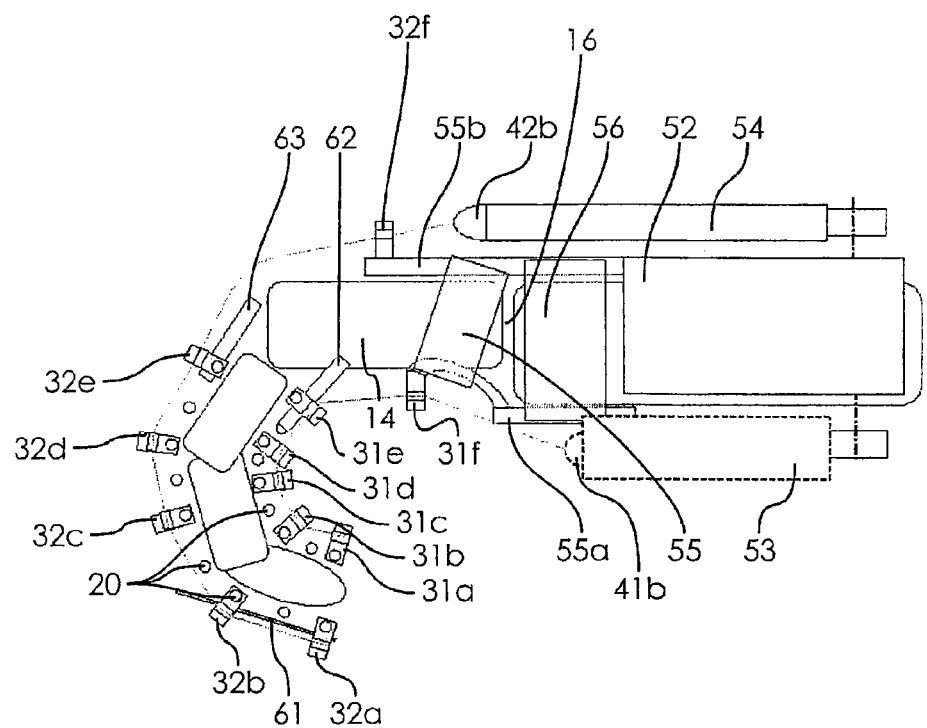
FIG. 5 is a side view showing a structure of the apparatus in its bent state.

FIG. 4 is a side view showing a structure of a finger motion assisting apparatus according to another embodiment in its stretched state. FIG. 5 is a side view showing a structure of the apparatus in its bent state. The same constituent elements as those of the previous embodiment are designated with the same symbols, and explanation thereof will be omitted.

The finger motion assisting apparatus of the embodiment includes a wrist fixing tool 55 for restricting a joint motion of a wrist 16. The wrist fixing tool 55 is fixed to the arm plate 52. As shown in the drawings, it is preferable that a palm-side support member 55a and a back-side support member 55b of the wrist fixing tool 55 are attached to the front arm by means of a belt 56.

According to the apparatus of the embodiment, a wire guide 31e through which the first wire 41 is inserted, and a wire guide 32e through which the second wire 42 is inserted are provided at positions of the proximal phalanx 13 on the side of the metacarpal bone 14. The wrist fixing tool 55 includes a first wire guide 31f for the wrist fixing tool through which the first wire 41 is inserted and a second wire guide 32f for the wrist fixing tool through which the second wire 42 is inserted.

In the apparatus of the embodiment, a reinforcing member 62 is provided on the side of the palm and a reinforcing member 63 is provided on the back side astride the joint between the proximal phalanx 13 and the metacarpal bone 14.

According to the finger motion assisting apparatus of the embodiment, the wire guides 31e and 32e are provided at positions of the proximal phalanx 13 on the side of the metacarpal bone 14, and the first wire guide 31f and the second wire guide 32f for the wrist fixing tool are provided at positions of the wrist fixing tool 55. With this, the proximal phalanx 13 can bend as shown in FIG. 5.

When the finger motion assisting apparatus of the embodiment is integrally formed together with a glove by the reinforcing members 62 and 63, stresses of attaching and driving can be moderated by an elastic root.

Next, another embodiment of the finger motion assisting apparatus of the invention will be explained.

Figure 6:
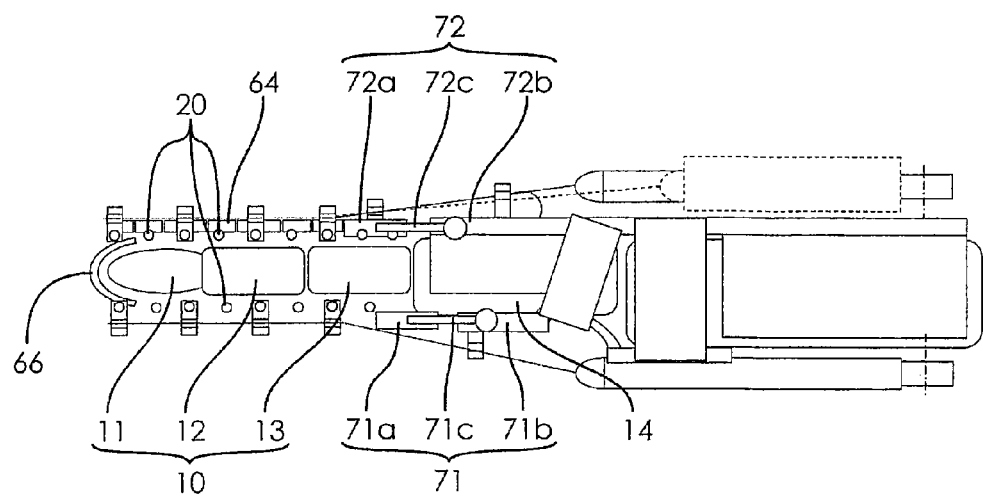
FIG. 6 is a side view showing a structure of a finger motion assisting apparatus according to another embodiment of the invention in its stretched state.
Figure 7:
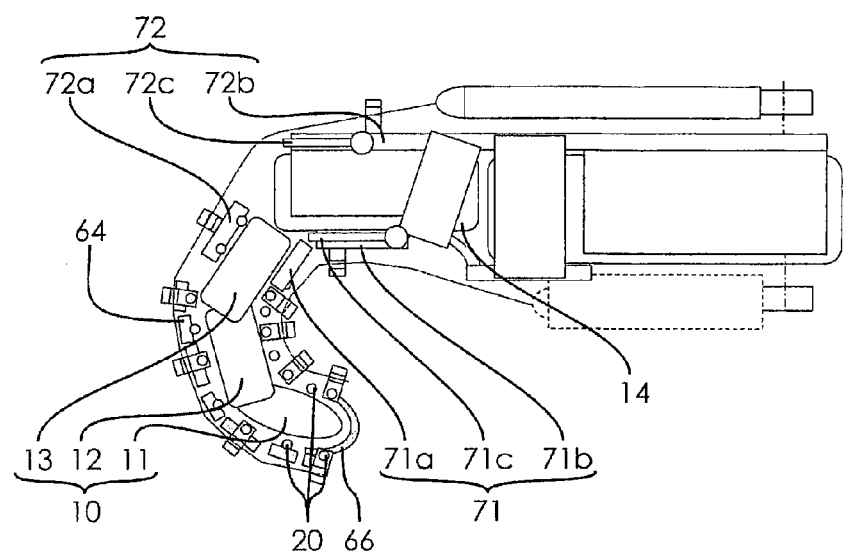
FIG. 7 is a side view showing a structure of the apparatus in its bent state when a joint lock mechanism is released.
Figure 8:
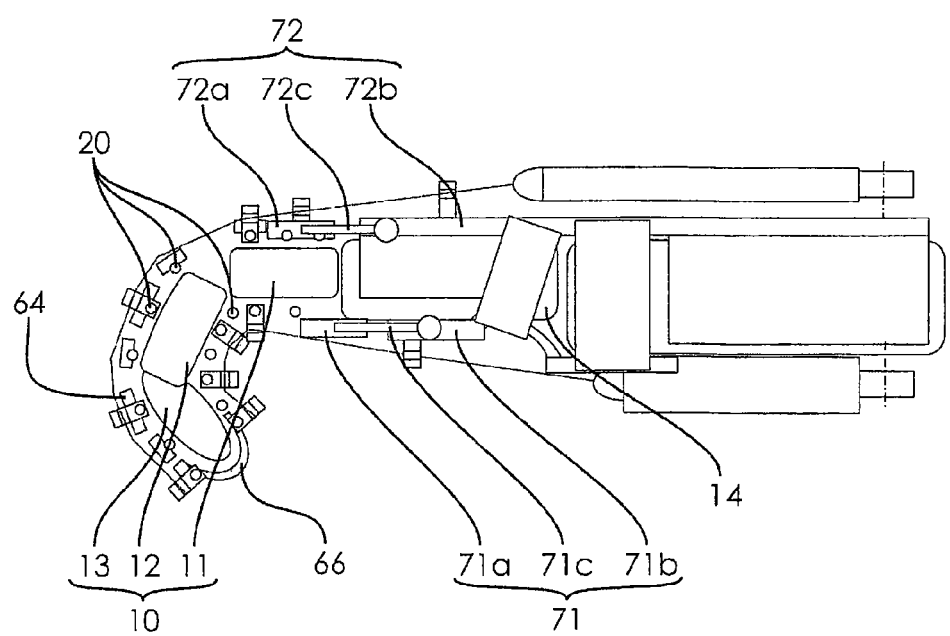
FIG. 8 is a side view showing a structure of the apparatus in its bent state when the joint lock mechanism functions.

FIG. 6 is a side view showing a structure of a finger motion assisting apparatus according to the embodiment in its stretched state. FIG. 7 is a side view showing a structure of the apparatus in its bent state when a joint lock mechanism is released. FIG. 8 is a side view showing a structure of the apparatus in its bent state when the joint lock mechanism functions. The same constituent elements as those of the previous embodiment are designated with the same symbols, and explanation thereof will be omitted.

In the finger motion assisting apparatus of the embodiment, a compression/warp-preventing member 64 is used instead of the warp-preventing member 61 shown in FIGS. 1 to 5, a cap 66 that is effective for dispersing a pressure applied to a tip end of a finger is provided on the tip end of the finger, and joint lock mechanisms 71 and 72 are used instead of the reinforcing members 62 and 63 shown in FIGS. 4 and 5.

The compression/warp-preventing member 64 of the embodiment includes a plurality of fixing units, and these fixing units are provided on the back sides of the phalanxes 10. A plurality of bridge members are arranged on the back side of the finger holding members 20 like compression springs at predetermined distances from one another, the fixing units are respectively provided on the bridge members, thereby constituting the compression/warp-preventing member 64. In this case, when the finger holding member 20 stretches as shown in FIG. 6, the fixing units provided on the bridge members are in abutment against each other. In this embodiment, the compression spring itself constituting the finger holding member 20 constitutes a movable unit that connects the fixing units with each other.

Although the compression/warp-preventing member 64 is provided in this embodiment, if a shape and a distance of the wire guide group 32 on the back side of the finger are adjusted, the wire guide group 32 can function as the compression/warp-preventing mechanism.

The joint lock mechanism 71 is provided astride the third joint on the palm side of the third joint between the proximal phalanx 13 and the metacarpal bone 14. The joint lock mechanism 71 includes a palm-side member 71a on the side of the proximal phalanx 13, a palm-side member 71b on the side of the metacarpal bone 14, and a connecting member 71c that connects and disconnects the palm-side member 71a and the palm-side member 71b with and from each other.

In a state where the connection between the palm-side member 71a and the palm-side member 71b is released by the connecting member 71c, the joint lock mechanism 71 releases the bending restriction of the proximal phalanx 13 with respect to the metacarpal bone 14 as shown in FIG. 7. In a state where the palm-side member 71a and the palm-side member 71b are connected by the connecting member 71c, the joint lock mechanism 71 restricts the proximal phalanx 13 such that it does not bend toward the palm side with respect to the metacarpal bone 14 more than the predetermined angle as shown in FIG. 8. The palm-side member 71a and the palm-side member 71b are connected to and disconnected from each other by sliding the connecting member 71c.

The joint lock mechanism 72 is provided astride the third joint on the back side of the third joint between the proximal phalanx 13 and the metacarpal bone 14. The joint lock mechanism 72 includes a back-side member 72a on the side of the proximal phalanx 13, a back-side member 72b on the side of the metacarpal bone 14, and a connecting member 72c that connects and disconnects the back-side member 72a and the back-side member 72b with and from each other.

In a state where the connection between the back-side member 72a and the back-side member 72b is released by the connecting member 72c, the joint lock mechanism 72 releases the bending-restriction of the proximal phalanx 13 with respect to the metacarpal bone 14 as shown in FIG. 7, and in a state where the back-side member 72a and the back-side member 72b are connected to each other by the connecting member 72c, the joint lock mechanism 72 restricts the proximal phalanx 13 such that it does not bend backward with respect to the metacarpal bone 14 more than the predetermined angle as shown in FIG. 8. The back-side member 72a and the back-side member 72b are connected to and disconnected from each other by sliding the connecting member 72c.

Next, another embodiment of the finger motion assisting apparatus of the invention will be explained.

Figure 9:
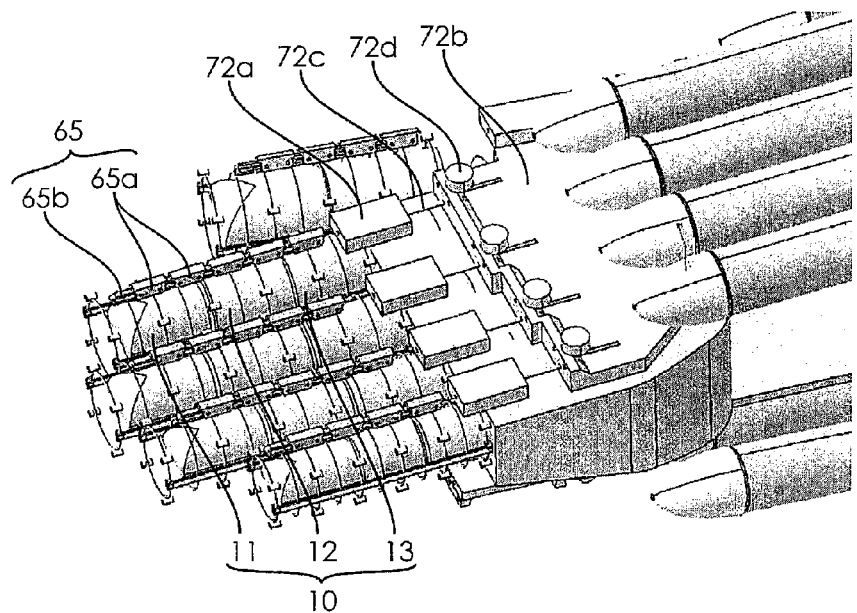
FIG. 9 is a perspective view showing a locked state of a back-side joint lock mechanism of a finger motion assisting apparatus according to another embodiment of the invention.
Figure 10:
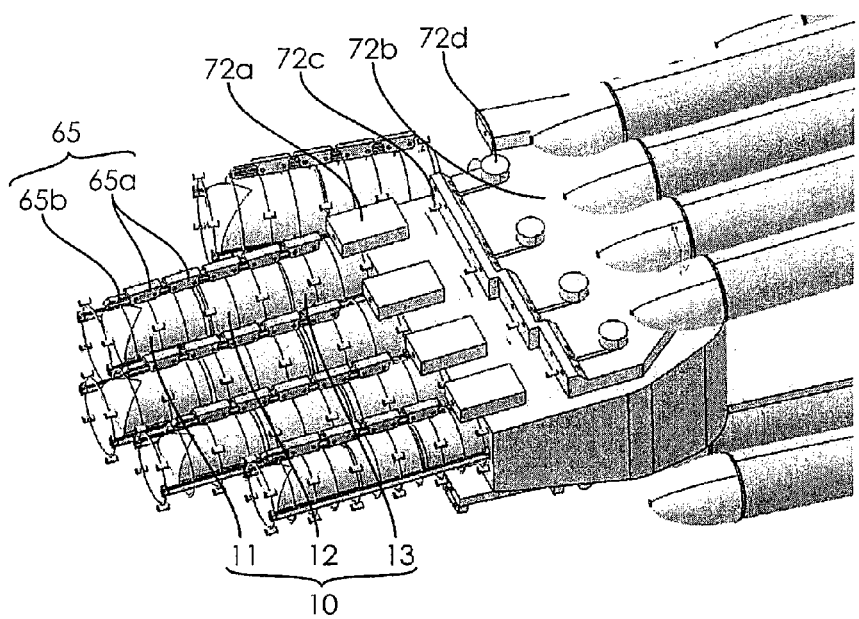
FIG. 10 is a perspective view showing the lock mechanism in its released state.
Figure 11:
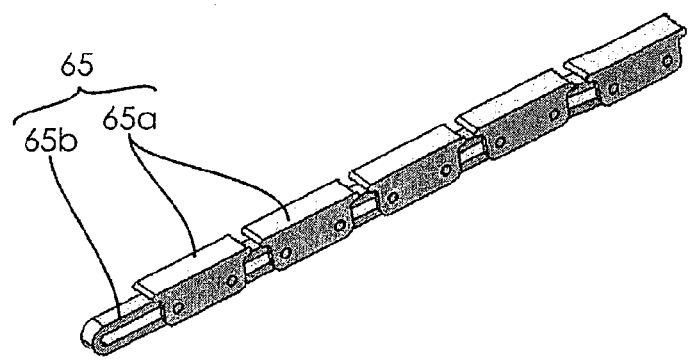
FIG. 11 is a perspective view of a compression/warp-preventing member of the apparatus in its stretched state.
Figure 12:
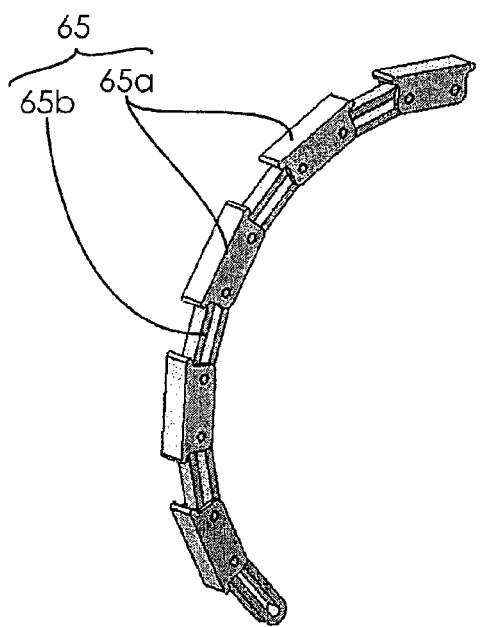
FIG. 12 is a perspective view of the compression/warp-preventing member in its bent state.

FIG. 9 is a perspective view showing a locked state of a back-side joint lock mechanism of a finger motion assisting apparatus according to this embodiment. FIG. 10 is a perspective view showing a released state of the lock mechanism. FIG. 11 is a perspective view showing a stretched state of a warp-preventing member of the apparatus. FIG. 12 is a perspective view showing the warp-preventing member in its bent state. The same constituent elements as those of the previous embodiment are designated with the same symbols, and explanation thereof will be omitted.

According to the finger motion assisting apparatus of this embodiment, connection and disconnection of the joint lock mechanism 72 shown in FIGS. 6 to 8 can independently be carried out for each of fingers. Lock pins 72d are provided on ends of the respective connecting members 72c on the side of the back-side member 72b. The back-side members 72a are independently constituted for the respective fingers. Connection and disconnection are carried out by the connecting member 72c by operating the lock pin 72d.

The finger motion assisting apparatus of the embodiment uses a compression/warp-preventing member 65 instead of the compression/warp-preventing member 64 shown in FIGS. 6 to 8.

The compression/warp-preventing member 65 of the embodiment includes a plurality of fixing units 65a and a movable unit 65b that connects the fixing units 65a with each other. The compression/warp-preventing member 65 restricts the backward bending motion of the phalanxes 10 caused by interference between the fixing units 65a.

Next, another embodiment of the finger motion assisting apparatus of the invention will be explained.

Figure 13:
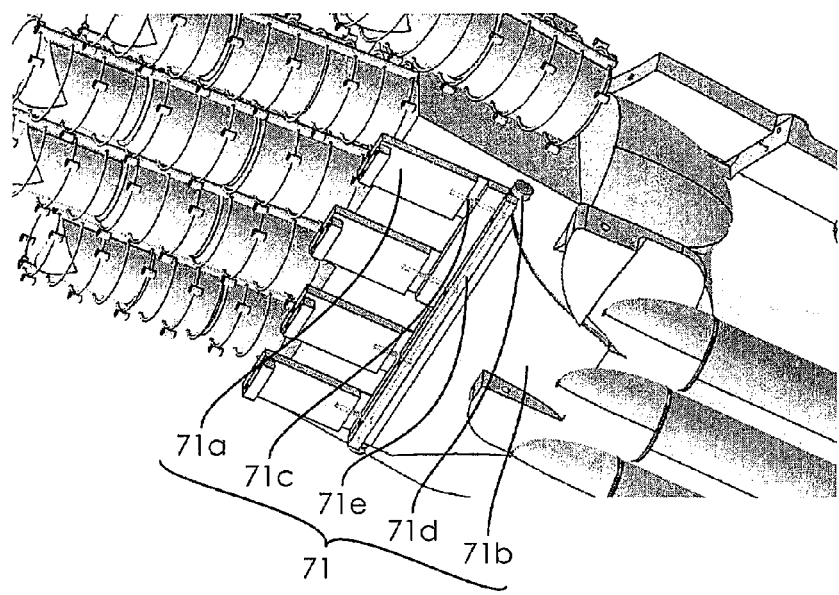
FIG. 13 is a perspective view of a palm-side joint lock mechanism of a finger motion assisting apparatus according to another embodiment of the invention in its locked state.
Figure 14:
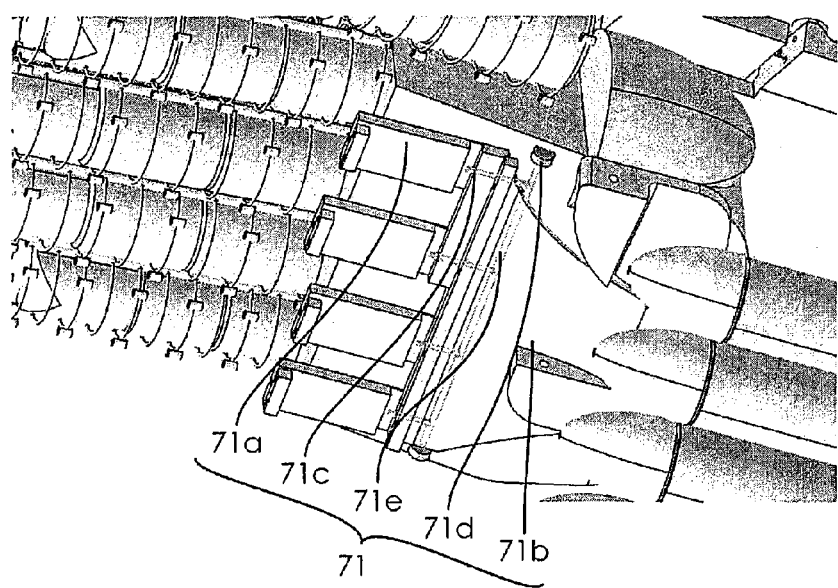
FIG. 14 is a perspective view showing the lock mechanism in its released state.

FIG. 13 is a perspective view showing a palm-side joint lock mechanism of the finger motion assisting apparatus of the embodiment in its locked state. FIG. 14 is a perspective view showing the lock mechanism in its released state. The same constituent elements as those of the previous embodiment are designated with the same symbols, and explanation thereof will be omitted.

According to the finger motion assisting apparatus of the embodiment, the connection and disconnection of the joint lock mechanism 71 shown in FIGS. 6 to 8 can be carried out for each of all fingers at the same time. Ends of the connecting members 71c on the side of the palm-side member 71b are connected a connecting rod 71e, and a lock pin 71d is provided on the connecting rod 71e. Connection and disconnection by all of the connecting members 71c can be carried out at the same time by operation of the lock pin 71d.

Next, another embodiment of the finger motion assisting apparatus of the invention will be explained.

Figure 15:
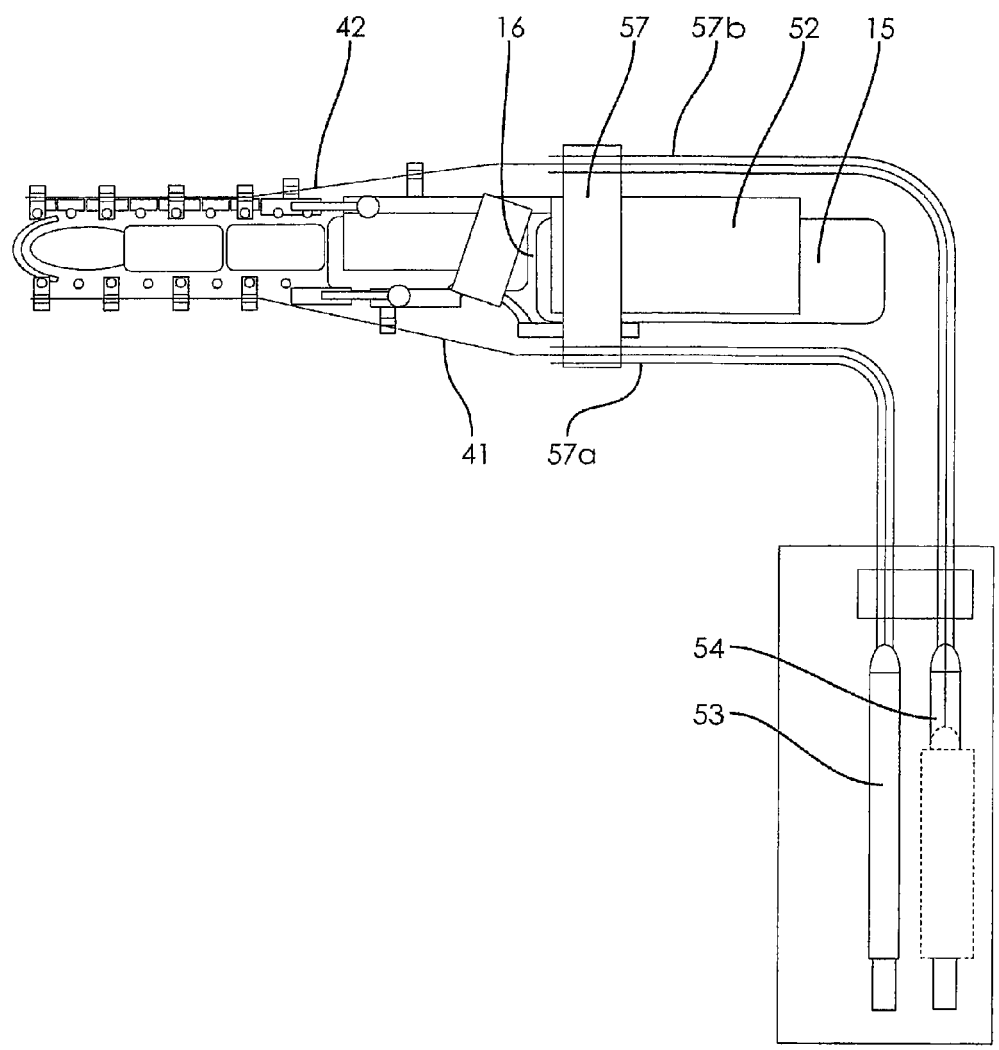
FIG. 15 is a side view of a structure of a finger motion assisting apparatus according to another embodiment of the invention.

FIG. 15 is a side view showing a structure of the finger motion assisting apparatus of the embodiment. The same constituent elements as those of the previous embodiment are designated with the same symbols, and explanation thereof will be omitted.

According to the finger motion assisting apparatus of the embodiment, a wire fixing tool 57 is provided on the front arm 15 on the side of the wrist 16, the driving units 53 and 54 are removed from the arm plate 52, and they are disposed at a brachium or other locations.

The wire fixing tool 57 includes sleeve holding portions 57a and 57b, the first wire 41 and the second wire 42 are inserted through the sleeve holding portions 57a and 57b, and they are connected to the driving units 53 and 54. With this, fixing at the palm or wrist can be eliminated.

Next, another embodiment of the finger motion assisting apparatus of the invention will be explained.

Figure 16:
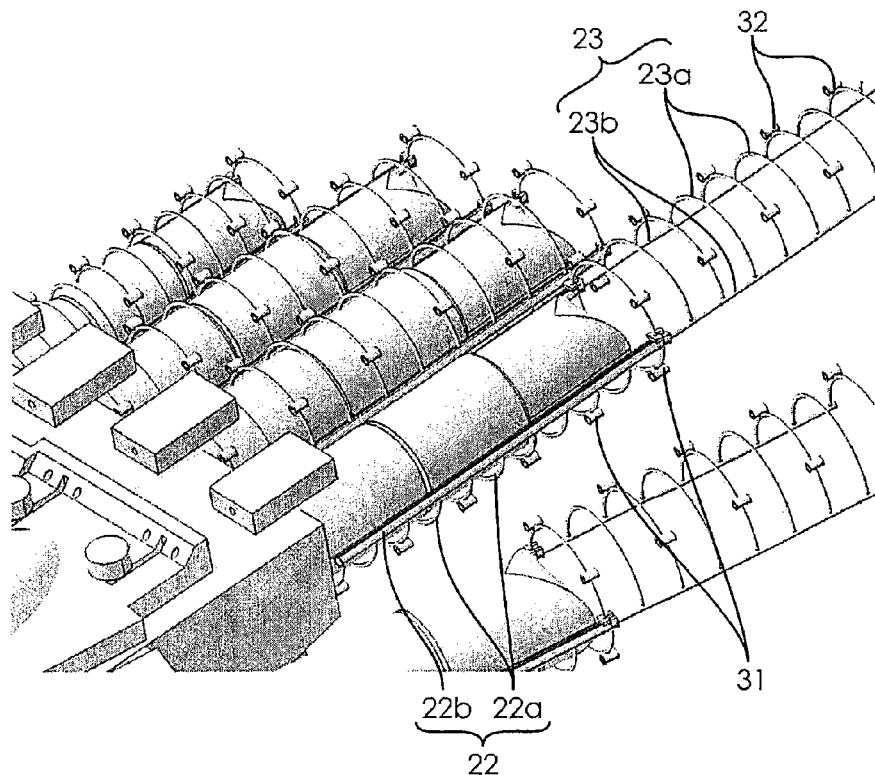
FIG. 16 is a perspective view showing a wearing state of a finger holding member of a finger motion assisting apparatus according to another embodiment of the invention.
Figure 17:
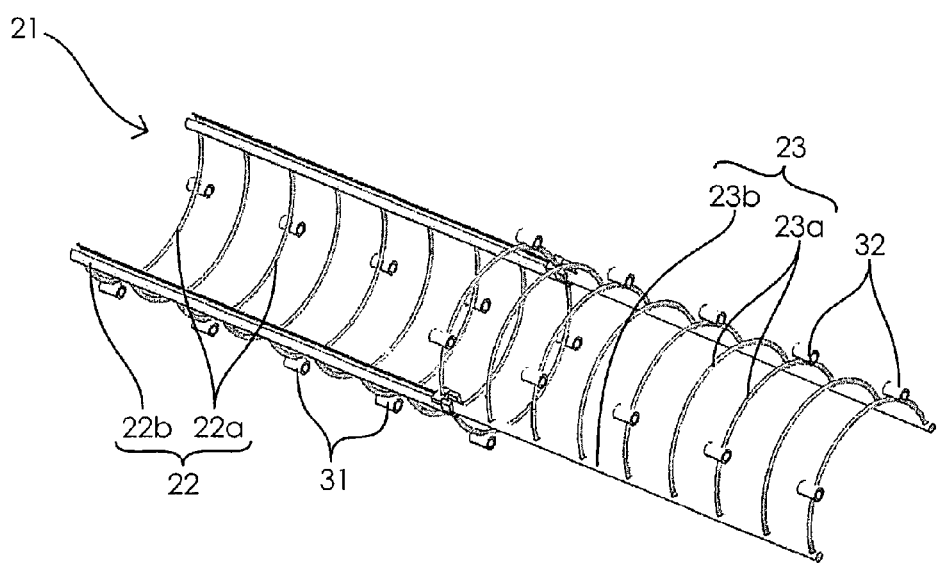
FIG. 17 is a perspective view showing a state before wearing the finger holding member.
Figure 18:
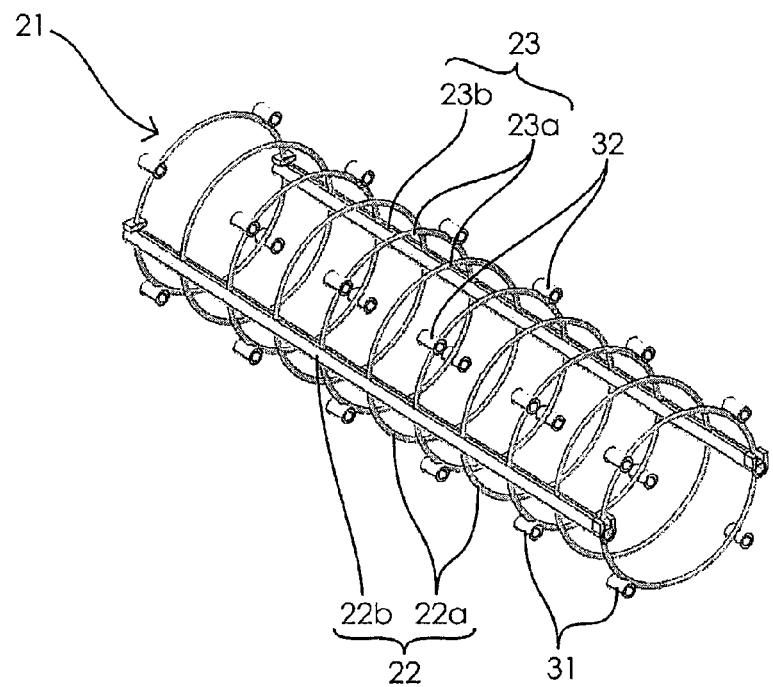
FIG. 18 is a perspective view showing a state after wearing the finger holding member.
Figure 19:
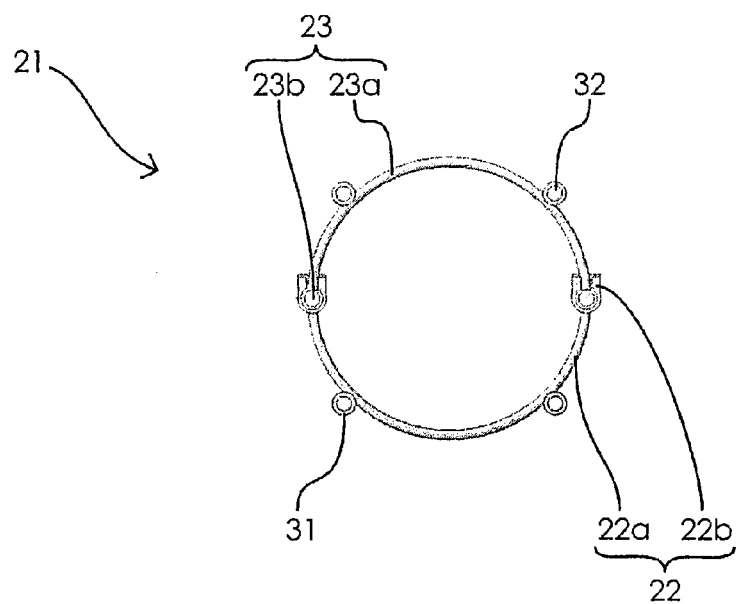
FIG. 19 is a front view of the finger holding member.
Figure 20:
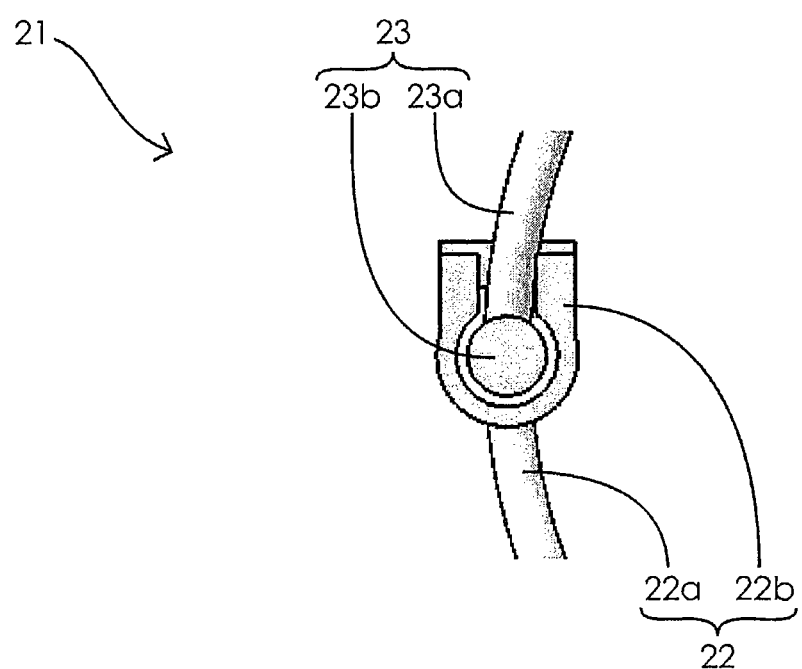
FIG. 20 is an enlarged view of an essential portion in FIG. 19.

FIG. 16 is a perspective view showing a wearing state of a finger holding member of the finger motion assisting apparatus of the embodiment. FIG. 17 is a perspective view showing a state before wearing the finger holding member. FIG. 18 is a perspective view showing a state after wearing the finger holding member. FIG. 19 is a front view of the finger holding member. FIG. 20 is an enlarged view of an essential portion in FIG. 19. The same constituent elements as those of the previous embodiment are designated with the same symbols, and explanation thereof will be omitted.

The finger holding member 21 of the finger motion assisting apparatus of the embodiment includes a palm-side finger holding member 22 disposed on the palm side of the phalanxes 10, and a back-side finger holding member 23 disposed on the back side of the phalanxes 10. The palm-side finger holding member 22 includes a plurality of bridge members 22a having the first wire guide group 31, and a pair of connecting members 22b connecting ends of the bridge members 22a with each other. The back-side finger holding member 23 includes a plurality of bridge members 23a having the second wire guide group 32, and a pair of connecting members 23b connecting ends of the bridge members 23a with each other.

Spring wires are used as the bridge members 22a and 23a in this embodiment, but they are not limited only if they can hold the fingers, and the bridge members may be of a slit type. If the spring wires are used, the amount of material thereof can be reduced, restraint of the connecting member 23b can be reduced, and the spring wire is less prone to hinder the bending motion.

A wire made of elastic material is used as the connecting member 23b constituting the back-side finger holding member 23. The connecting member 22b constituting the palm-side finger holding member 22 is a C-shaped pipe having an inner diameter that is greater than an outer diameter of the wire of the connecting member 23b. A spring wire, elastic material such as resin, an extension spring having a small winding diameter, and a compression spring can be used as the connecting member 22b and the connecting member 23b.

In this embodiment, the connecting member 22b constituting the palm-side finger holding member 22 is a C-shaped pipe, the wire is used as the connecting member 23b constituting the back-side finger holding member 23. With this, the back-side finger holding member 23 can slide with respect to the palm-side finger holding member 22, and the back-side finger holding member 23 can be attached and detached.

According to the embodiment, the finger can be covered with the back-side finger holding member 23 after the finger is placed on the palm-side finger holding member 22, and it is easy to attach the apparatus.

Next, another embodiment of the finger motion assisting apparatus will be explained.

Figure 21:
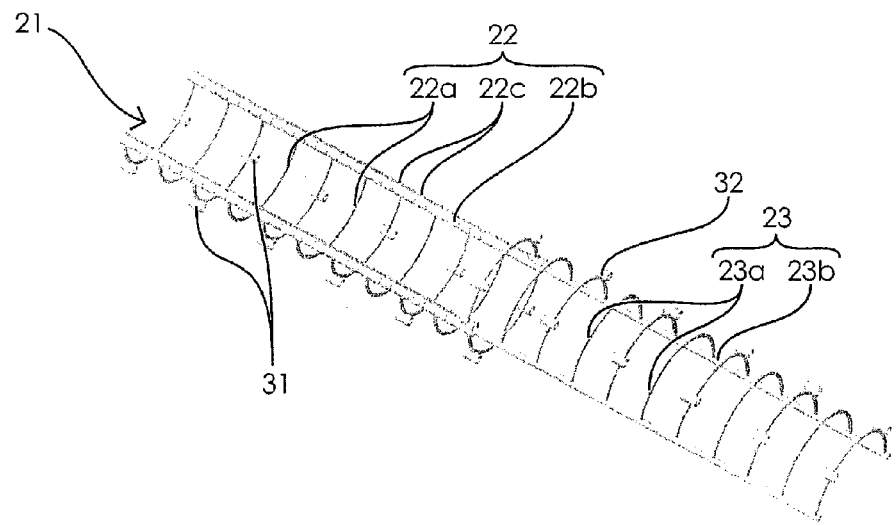
FIG. 21 is a perspective view showing a state before wearing the finger holding member of a finger motion assisting apparatus according to another embodiment of the invention.
Figure 22:
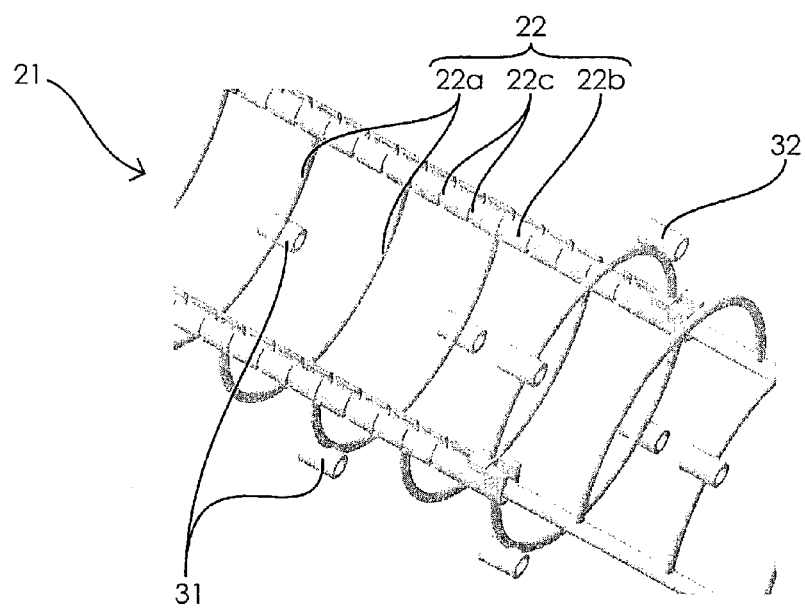
FIG. 22 is an enlarged view of an essential portion in FIG. 21.

FIG. 21 is a perspective view showing a state before wearing the finger holding member of the finger motion assisting apparatus of the embodiment. FIG. 22 is an enlarged view of an essential portion in FIG. 21. The same constituent elements as those of the previous embodiment are designated with the same symbols, and explanation thereof will be omitted.

In the finger holding member 21 of the finger motion assisting apparatus of the embodiment, a plurality of slits 22c are formed in the connecting member 22b made of an elastic material of the palm-side finger holding member 22 disposed on the palm side of the phalanxes 10. The slits 22c are formed in a direction perpendicular to an axis of the connecting member 22b.

According to the embodiment, the connecting member 22b is formed from a C-shaped pipe, the plurality of slits 22c are provided and with this, bending characteristics can be enhanced.

Next, another embodiment of the finger motion assisting apparatus will be explained.

Figure 23:
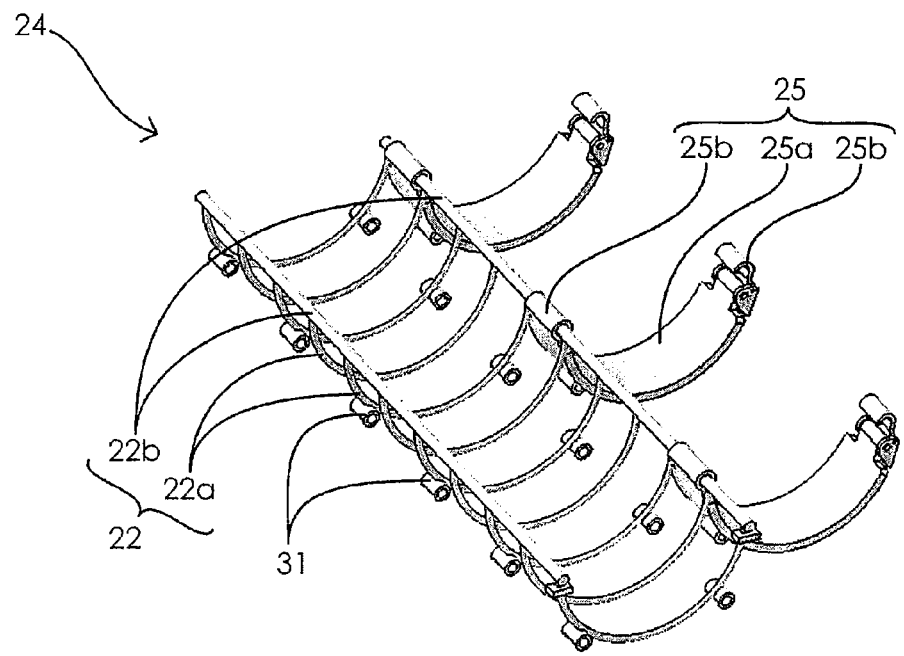
FIG. 23 is a perspective view showing a state before wearing the finger holding member of a finger motion assisting apparatus according to another embodiment of the invention.
Figure 24:
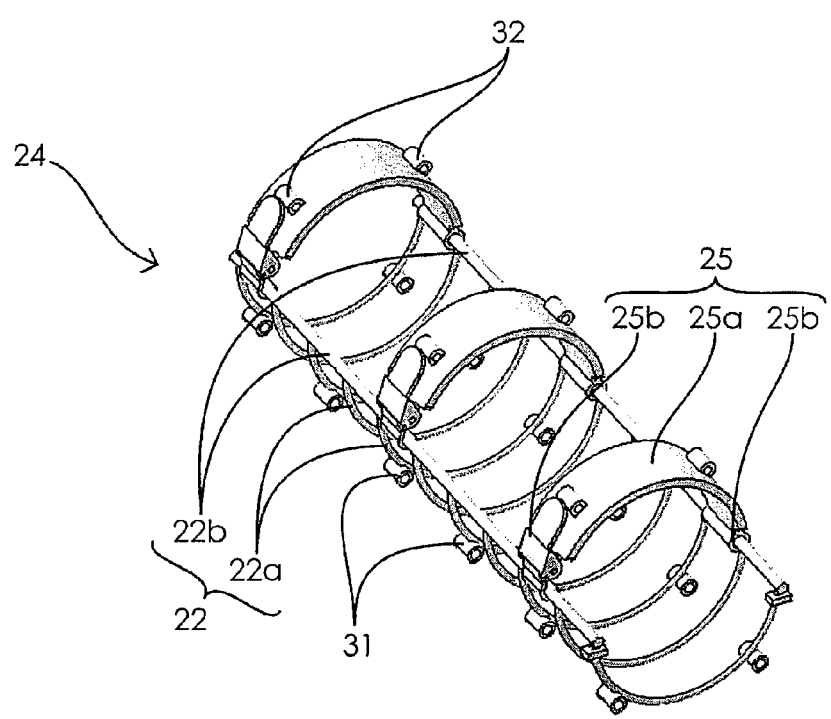
FIG. 24 is a perspective view showing a state after wearing the finger holding member.

FIG. 23 is a perspective view showing a state before wearing the finger holding member of the finger motion assisting apparatus of the embodiment. FIG. 24 is a perspective view showing a state after wearing the finger holding member. The same constituent elements as those of the previous embodiment are designated with the same symbols, and explanation thereof will be omitted.

A finger holding member 24 of the finger motion assisting apparatus of the embodiment includes a palm-side finger holding member 22 disposed on the palm side of the phalanxes 10, and a back-side finger holding member 25 disposed on the back side of the phalanxes 10. The palm-side finger holding member 22 includes a plurality of bridge members 22a having the first wire guide group 31, and a pair of connecting member 22b connecting ends of the bridge members 22a. The back-side finger holding member 25 includes a plurality of bridge members 25a having the second wire guide group 32, and a pair of connecting members 25b connecting ends of the bridge members 25a.

In this embodiment, a spring wire is used as the bridge member 22a, and an arch material having a predetermined width is used as the bridge member 25a. A wire is used as the connecting member 22b constituting the palm-side finger holding member 22. The connecting member 25b constituting the back-side finger holding member 25 includes a pipe and a hook that can turn around a wire made of elastic material of the connecting member 22b.

According to the embodiment, the wearing feeling and productivity are excellent.

In each of the embodiments, the wearing feeling can further be enhanced by fixing the finger holding member 20, the palm plate 51 or the wrist fixing tool 55 to a glove.

The present invention can be utilized as a finger motion assisting apparatus that assists a bending and stretching motion of a finger of a user's hand.

What is claimed is:

1. A finger motion assisting apparatus for assisting the motion of a finger comprising:
a finger holding member configured to be disposed on an outer periphery of phalanxes including a distal phalanx, a middle phalanx and a proximal phalanx, the finger holding member comprising a spring-like member configured to encircle the outer periphery of the phalanxes, such that a neutral axis of the spring matches with a center axis of the finger to be assisted;

a wire guide group provided on the finger holding member;
a wire inserted through the wire guide group; and
a driving unit that pulls or loosens the wire, with which the finger motion assisting apparatus is configured to bend and stretch the phalanxes, the driving unit comprising an artificial muscle that extends and contracts along a longitudinal length of the finger by supplying or discharging a gas, a liquid, a solid material, or a mixture thereof, wherein
the wire guide group comprises a first wire guide group configured to be located on a palm side of the phalanxes, and a second wire guide group configured to be located on a back side of the phalanxes,
the wire is fixed to the finger holding member configured to be disposed on the distal phalanx,
the wire comprises a first wire inserted through the first wire guide group, and a second wire inserted through the second wire guide group,
the driving unit loosens the first wire when the second wire is pulled in a stretched state, and
the driving unit loosens the second wire when the first wire is pulled such that a shape of the spring-like member is changed from the shape of the spring-like member in the stretched state, such that a portion of the spring-like member on the palm side is compressed and a portion of the spring-like member on the back side is stretched in a bent state.

2. The finger motion assisting apparatus according to claim 1, wherein the finger holding member comprises a palm-side finger holding member disposed on the palm side of the phalanxes, and a back-side finger holding member disposed on the back side of the phalanxes,
each of the palm-side finger holding member and the back-side finger holding member comprises a plurality of bridge members having the wire guide group, and a pair of connecting members connecting ends of the bridge members with each other, and the connecting member constituting the palm-side finger holding member and the connecting member constituting the back-side finger holding member can be attached to and detached from each other.

3. The finger motion assisting apparatus according to claim 2, wherein an elastic material is used as the connecting member.

4. The finger motion assisting apparatus according to claim 2, wherein the connecting member constituting the palm-side finger holding member and the connecting member constituting the back-side finger holding member are made of elastic material, a wire is used as one of the connecting members, and a C-shaped pipe having an inner diameter that is greater than an outer diameter of the wire is used as the other connecting member.

5. The finger motion assisting apparatus according to claim 4, wherein a plurality of slits are formed in the other connecting member in a direction perpendicular to an axis of the other connecting member.

6. The finger motion assisting apparatus according to claim 1, wherein the first wire guide group and the second wire guide group constitute a plurality of rows, and the first wire and the second wire are disposed in correspondence with the respective rows.

7. The finger motion assisting apparatus according to claim 1, wherein at least one wire guide constituting the wire guide group is provided in correspondence with each of the distal phalanx, the middle phalanx and the proximal phalanx.

8. The finger motion assisting apparatus according to claim 1, wherein a warp-preventing member is provided on the finger holding member disposed on a back side of a first joint between the distal phalanx and the middle phalanx astride the first joint, and the warp-preventing member restricts the distal phalanx such that the distal phalanx does not bend backward more than a predetermined angle with respect to the middle phalanx.

9. The finger motion assisting apparatus according to claim 1, wherein a warp-preventing member is provided on the finger holding member disposed on a back side of a second joint between the middle phalanx and the proximal phalanx astride the second joint, and the warp-preventing member restricts the middle phalanx such that the middle phalanx does not bend backward more than a predetermined angle with respect to the proximal phalanx.

10. The finger motion assisting apparatus according to claim 1, wherein a compression/warp-preventing member is provided on the finger holding member astride a joint of the phalanxes, the compression/warp-preventing member comprises a plurality of fixing units and a movable unit connecting the fixing units with each other, the compression/warp-preventing member restricts a backward bending motion of the phalanxes caused by interference between the fixing units, and restricts compression toward a metacarpal bone with respect to the phalanxes.

11. The finger motion assisting apparatus according to claim 1, wherein a joint lock mechanism is provided on at least one of a back side and a palm side of a third joint between the proximal phalanx and a metacarpal bone astride the third joint, and the joint lock mechanism restricts the proximal phalanx such that the proximal phalanx does not bend toward the palm side more than a predetermined angle with respect to the metacarpal bone.

12. The finger motion assisting apparatus according to claim 11, wherein the bending restriction of the proximal phalanx with respect to the metacarpal bone is released by moving the joint lock mechanism toward the metacarpal bone.

13. The finger motion assisting apparatus according to claim 1, further comprising a plate for supporting a metacarpal bone, and a joint lock mechanism connected to the plate between the proximal phalanx and the plate, wherein the joint lock mechanism restricts the proximal phalanx such that the proximal phalanx does not bend toward the palm side more than a predetermined angle with respect to the metacarpal bone.

14. The finger motion assisting apparatus according to claim 13, wherein the bending restriction of the proximal phalanx with respect to the metacarpal bone is released by releasing the connection between the joint lock mechanism and the plate.

15. The finger motion assisting apparatus according to claim 1, further comprising a wrist fixing tool for restricting a joint motion of a wrist, wherein the wrist fixing tool comprise a first wire guide for the wrist fixing tool through which the first wire is inserted, and a second wire guide for the wrist fixing tool through which the second wire is inserted.

16. The finger motion assisting apparatus according to claim 1, wherein a warp-preventing member is provided on the finger holding member disposed on a back side of a first joint between the distal phalanx and the middle phalanx astride the first joint and such that the finger holding member is prevented to compress at a position where the warp-preventing member is provided.

* * * * *